United States Patent [19]

Van Beek et al.

[11] Patent Number: 4,533,352
[45] Date of Patent: Aug. 6, 1985

[54] MICROSURGICAL FLEXIBLE SUCTION MAT

[75] Inventors: Allen L. Van Beek, Minneapolis; Alfred L. Iversen, Minnetonka, both of Minn.

[73] Assignee: PMT Inc., Hopkins, Minn.

[21] Appl. No.: 472,757

[22] Filed: Mar. 7, 1983

[51] Int. Cl.³ .............................................. A61M 1/00
[52] U.S. Cl. .................................... 604/317; 604/357; 604/313
[58] Field of Search ............. 128/134, 303 R; 269/15, 269/21, 327; 15/310, 311; 604/317, 73, 289, 313, 268, 315, 316, 356, 357

[56] References Cited

U.S. PATENT DOCUMENTS

| | | | |
|---|---|---|---|
| 3,165,773 | 1/1965 | Palpacelli | 15/310 |
| 3,286,693 | 11/1966 | Clarke, Jr. et al. | 128/134 |
| 3,307,818 | 3/1967 | Cocito | 269/21 |
| 3,783,863 | 1/1974 | Kliever | 128/134 |

Primary Examiner—C. Fred Rosenbaum
Assistant Examiner—J. L. Kruter
Attorney, Agent, or Firm—Hugh D. Jaeger

[57] ABSTRACT

Surgical suction mat including a rib, or the like, pliable member of a predetermined geometrical shape, a longitudinal cylindrical hose connected to the plurality of holes and being of a finite length including a suction hose connecton at the other end where the rib design with the holes provides suction to remove fluids oriented at an angle to the suction ports. The longitudinal cylindrical hose can include a parallel wire hose or the like to maintain a predetermined position. The ribbed design or the like of the pliable member allows drainage of fluids and lifts vessels, tissue or the like above the fluids. The ribbed pliable member is preferably opaque blue as a preferred color for working in a body tissue environment. The suction hose can be encompassing within the pliable member. The surgical suction mat can also be made of porous material with or without ribs.

11 Claims, 5 Drawing Figures

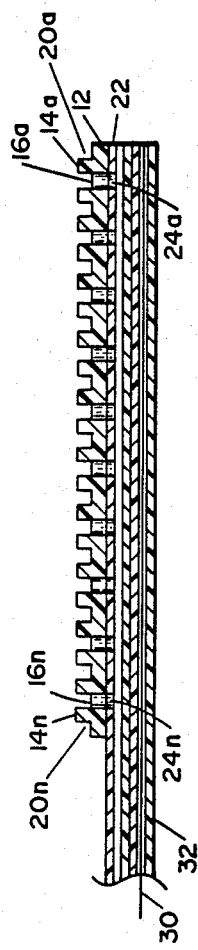
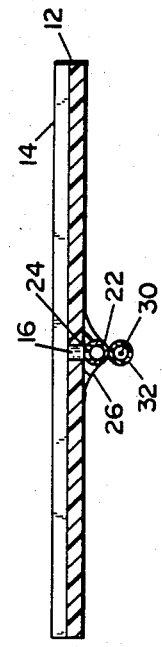
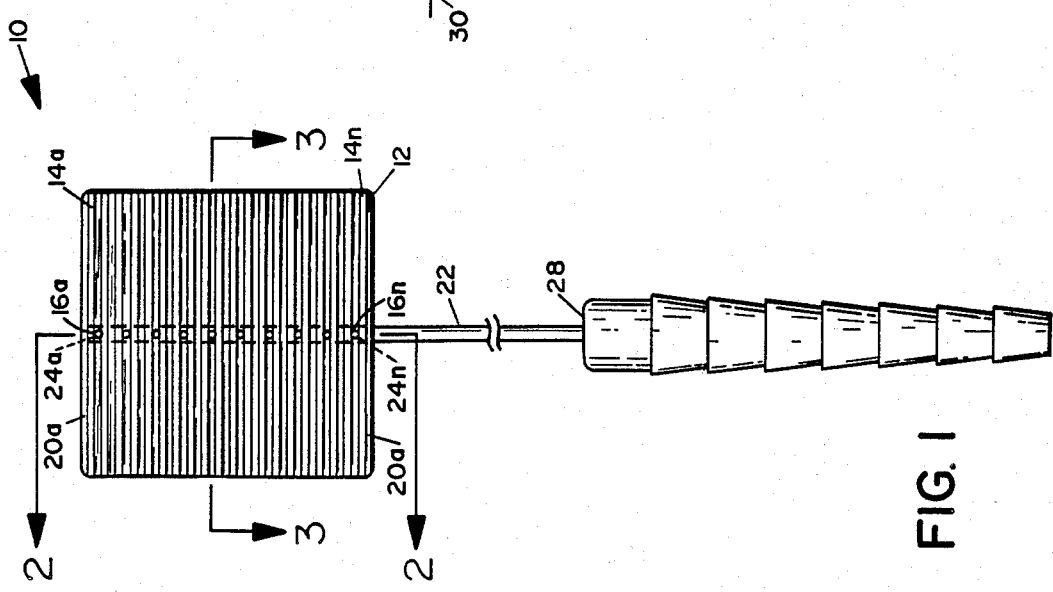
FIG. 2
FIG. 3
FIG. 1

MICROSURGICAL FLEXIBLE SUCTION MAT

BACKGROUND OF THE INVENTION

1. Field of the Invention

The present invention pertains to surgical instrumentation and, more particularly, pertains to a surgical mat for utilization in microsurgery and surgery in general.

2. Description of the Prior Art

Prior art instrument manufacturers have failed to provide suitable operating mats or pads which are sterile, disposable, and which provide for suction as well as an operating platform.

The prior art suction devices have usually been nothing more than a suction tube or the like for eliminating fluids during surgery. Microsurgery has been particularly difficult, in that during the surgical process a platform mat, or the like, has always been required on which to rest vessels, tissue or the like during the surgical process. The prior art problem has been that during the surgical process the tissues, vessels or the like would be limp, and in attempting to suture the vessels, tissue or the like at a particular junction, such as in anastomsis, the vessels would always tend to droop down at the place of suture. While crude prior art supports might have been utilized in the surgical theater, the supports would become a basin and platform for catching of fluids, such as blood or the like, making such surgery and suturing a most tedious and complicated procedure to even the most skilled surgeon in the operating theater.

The present invention overcomes the disadvantages of the prior art by providing a ribbed design center or end suction attachment with a malleable suction hose for evacuation of fluids.

SUMMARY OF THE INVENTION

The general purpose of the present invention is to provide a surgical suction unit with an opaque blue background, ribbed design, and a malleable suction hose for permitting placement and stability about background material during microsurgery, small surgery, or even generalized surgery as required. The unit is sterile and disposable, and can be manufactured in any length and diameter, and trimmed accordingly in the operating surgical theater to a specific size as desired by the attending surgeons. The device lends itself also to outpatient surgery as well as surgery in the field, such as in military use and the like.

According to one embodiment of the present invention, there is provided a pliable member such as that made of silicone rubber or the like, a plurality of ribs or other geometrical members extending upward therefrom, a plurality of holes through the pliable member, the holes being also designated as suction ports, and either being in line or in a predetermined geometrical pattern, a longitudinal cylindrical suction hose positioned below the pliable member, and having a like plurality of suction ports, the long cylindrical suction hose secured to the pliable members such as with silicone rubber or the like, and a suction hose connection at the other end for connection to a vacuum source whereby the rib design provides for drainage of fluids while additionally supporting vessels up above the fluids, the pliable mat member providing a location for stability of vessels, tissues, or the like during surgery. The suction tube through the suction ports removes fluids from the immediate area of operation, thereby providing location and stability for elimination of fluids from the operating environment. A wire can be extended through a longitudinal cylindrical hose parallel to the suction hose for additional stability and forming to a predetermined shape. The pliable mat member can take the predetermined geometrical shape of a rectangle, can be manufactured in a rectangle for subsequent cutting by the surgeon, or can be manufactured in other geometrical configuration such as squares, circles, ovals, elipses or the like. The preferred color of the pliable member, as against the color of body fluids and tissues, is a dark opaque blue. While a ribbed design has been designated, any other suitable geometrical configuration for supporting tissues while providing inner drainage of suction can be included, such as projecting dots, inline dots, circular ribs or the like. The suction and wire hose can be incorporated into the pliable mat member in an alternative embodiment.

According to another embodiment of the present invention, there is provided a porous material in the shape of a circular member having a finite height, a coating about the circumference of the circular member and the bottom, and a longitudinal cylindrical suction hose with parallel wire tube extending to the substantially center of the circular area but below the planar surface, for providing a rest and support for tissue and the like, but providing a porous member for fluids running down and being sucked out from the bottom of the porous member, which is coated to retain fluids.

One significant aspect and feature of the present invention is a surgical suction mat which can be manufactured in various lengths, diameters, and color of background, and is trimmable to a desired size in the surgical theater. While surgical suction ports can be provided on a longitudinal axis, the surgical suction ports can also be arranged in a circular configuration, an oval configuration, or any other like connecting configuration or nonconnecting configuration.

Another significant aspect and feature of the present invention is a surgical suction mat which is malleable, aiding in location and stability of suturing of vessels and tissues. The ribbed design provides for drainage of fluids in the surgical environment while lifting of vessels and tissues above the fluids so as to assist the surgeon and provide for least time and motion on the surgeon's behalf.

A further significant aspect and feature of the present invention is a ribbed texture on one side and a smooth texture on the reverse side.

An additional significant aspect and feature of the present invention is a surgical suction mat which is sterile and disposable, made of a material which is nonevasive to the body such as silicone rubber or the like, and colored opaque blue which is a preferred background material in the operating theater. Other possible colors include yellow, green, white, black or the like.

Having thus described embodiments of the present invention, it is a principal object hereof to provide a surgical suction mat.

One object of the present invention is to provide a surgical suction mat with a background color such as opaque blue, with built-in suction to remove fluids and oriented at right angles to suction ports. Malleable suction hoses aid in placement and stability of the pliable support mat member.

Another object of the present invention is a surgical suction mat which includes a plurality of geometrical projections for raising tissues and vessels up above the level of draining fluids.

A further object of the present invention is a surgical suction mat where the section hose is incorporated into the pliable mat structure.

An additional object of the present invention is a surgical suction mat where the pliable member is a porous member, with or without ribs, for supporting tissue vessels, nerves, or the like.

BRIEF DESCRIPTION OF THE DRAWINGS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 illustrates a plan view of a surgical suction mat, the present invention;

FIG. 2 illustrates a section view taken along line 2—2 of FIG. 1, along the axis of the suction ports;

FIG. 3 illustrates a view taken along line 3—3 of FIG. 1, along and parallel to the ribs and through a suction port;

DESCRIPTION OF PREFERRED EMBODIMENTS

Figure 4:
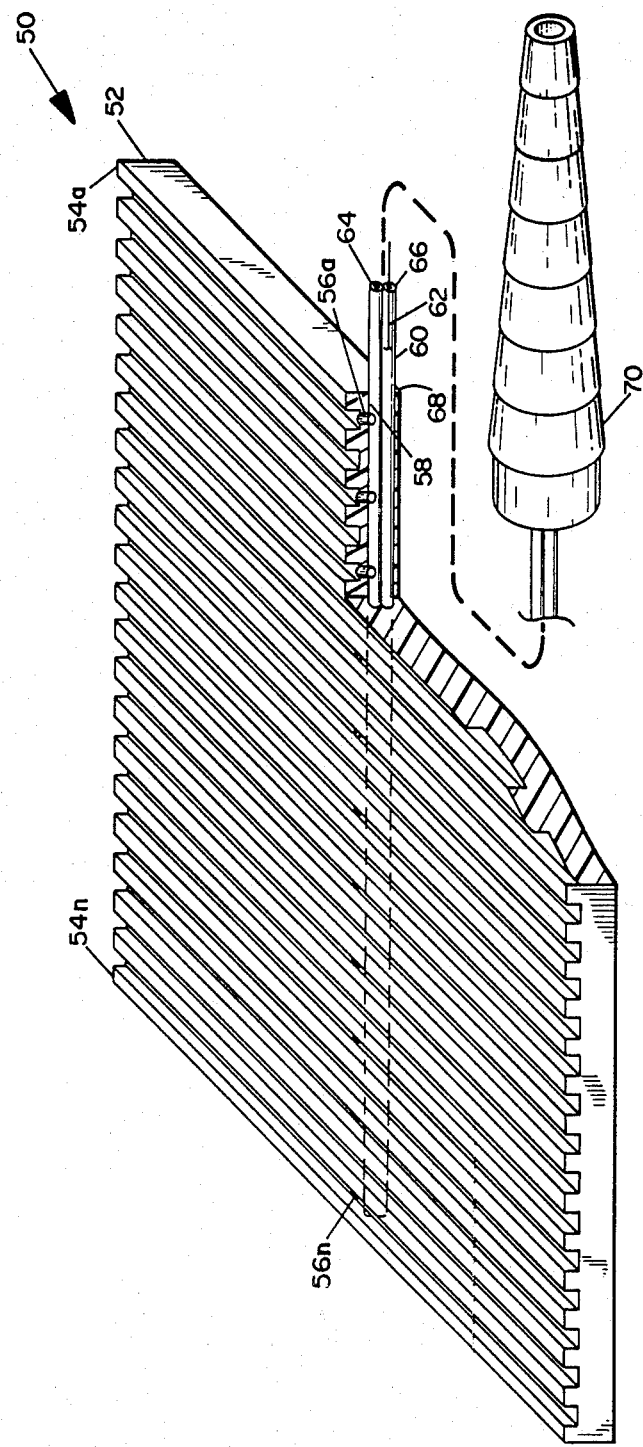
FIG. 4 illustrates an alternative embodiment of a surgical suction mat utilizing a suction hose and wire incorporated into a surgical suction mat; and, FIG. 5 illustrates an alternative embodiment of a surgical suction mat utilizing a pourous member.

FIG. 1 illustrates a plan view of a surgical suction mat 10, the present invention, showing a pliable mat member 12 which is illustrated as a square-rectangular member, by way of example and for purposes of illustration only, and not to be construed as limiting of the present invention, as the mat 12 can be circular, oval, eliptical, or of any other predetermined geometrical shape. The mat 12 can also be trimmed to any predetermined geometrical shape by the surgeon as long as the end of the suction hose of course is not trimmed, and in the alternative, a wide range of geometrical shapes as well as geometrical sizes. Extending upwardly from the mat 12 is a plurality of ribs 14a–14n which in this embodiment are parallel to each other and spaced a predetermined distance between each other at a finite height from the mat 12. In the alternative of ribs, a plurality of dots in line could be substituted, the dots could take circular groups of decreasing radius from a center of the mat 12, or could include any other like uprising geometrical members either positioned in spaced parallel configurations or a spaced geometrical configuration other than that on parallel axes. A plurality of holes or suction ports 16a–16n extend along a predetermined geometrical path entirely through the finite height of the mat 12 to an underside of the mat, these holes in this particular example are not to be construed as limiting thereof, on an axis which is substantially perpendicular to the parallel ribs 14a–14n. The suction ports 16a–16n could be arranged in a circular configuration, in a rectangular configuration, in an oval configuration, or in any other like configuration, dependent upon the particular type of surgery and the particular designated use by the surgeon. A finite space and gap 20a–20n as illustrated can be provided in each of the ribs to aid in the flow of fluid to the suction holes. A suction-like hose 22, which is a longitudinal cylindrical member, is secured below the surgical suction mat 10 and includes a like configuration and arrangement of holes 24a–24n. The hose 22 as illustrated in FIG. 3 is secured to the suction mat by any like process such as glueing with silicone cement 26 or in the alternative, the mat can be molded, heat-joined and fused or the like to the tubing. The cylindrical hose can be provided internal to the finite height of the mat, thereby providing a single combined mat 12-suction hose 22 in a single-member unit where the hose and holes would be encompassed within the finite height of the mat, as illustrated in alternative embodiment FIG. 4. The suction tube 22 extends longitudinally to a suction hose connection 28, A wire 30. can extend in a parallel molded hose 32 in conjunction with suction tube 22 and include wire 30 in the parallel tube for structural support and for maintaining a geometrical memory on formation.

FIG. 2 illustrates a section view taken along line 2—2 of FIG. 1, particularly showing the mat 12, the ribs 14a–14n, the suction ports 16a–16n, the suction tube 22, with suction holes 24a–24n in the suction tube, 22 and wire tube 32 with wire 30 inserted therein.

FIG. 3 illustrates a view taken along line 3—3 of FIG. 1 where all numerals correspond to those elements previously described.

MODE OF OPERATION

The surgical suction mat 10 is utilized by placing the pliable rib member under the surgical area, most commonly under vessels or arteries or the like, or such as nerves, to be reattached. Placement is augmented by the malleable suction wire 30 through the hose 32n , and connection is made by the suction hose connection 28 to a vacuum line in the surgical theater environment. Continuous suction and evacuation or controlled suction and evacuation provides for displacement of fluid through and about the rib designs, through the holes of the pliable member, through the holes of the tube and out through the vacuum system. Once fluids begin to flow and through fluid theory, those fluids will in effect pull other fluids behind as required during the suction procedure. The suction of fluids provides for less fatigue to the surgeon as well as providing least time and motion, and enhances the surgery in lifting the tissues, vessels, arteries or nerves above the fluids on the platform of the rib design or other predetermined geometrical members. The particular port of design can be either longitudinal as illustrated in this embodiment or can assume any other predetermined design such as circular, oval, eliptical or the like.

FIRST ALTERNATIVE EMBODIMENT

FIG. 4 illustrates an alternative embodiment 50 cutaway including a pliable mat 52, a plurality of ribs 54a–54n, a plurality of suction port holes 56a–56n, and a suction hose 58 through the length of the mat. The mat will assume a very low profile in finite height but illustrates the combination of a combined mat and suction structure providing an entirely planar structure.

Operation of the alternative embodiment is identical in fluid theory to that of FIGS. 1–3. The figure particulary illustrates the valleys between each of the ribs. Further, a wire support tube can be molded in below the suction hole-tube through the length of the mat where the wire support tube 60 supports a wire 62 as previously discussed. A suction-wire combined molded tube 64–66 extends from the end of the mat at exit-entry 68 to a hose connection 70. The suction tube 58-wire tube 60 can extend either partially through the mat 52 or entirely through the mat 52 as illustrated.

SECOND ALTERNATIVE EMBODIMENT

Figure 5:
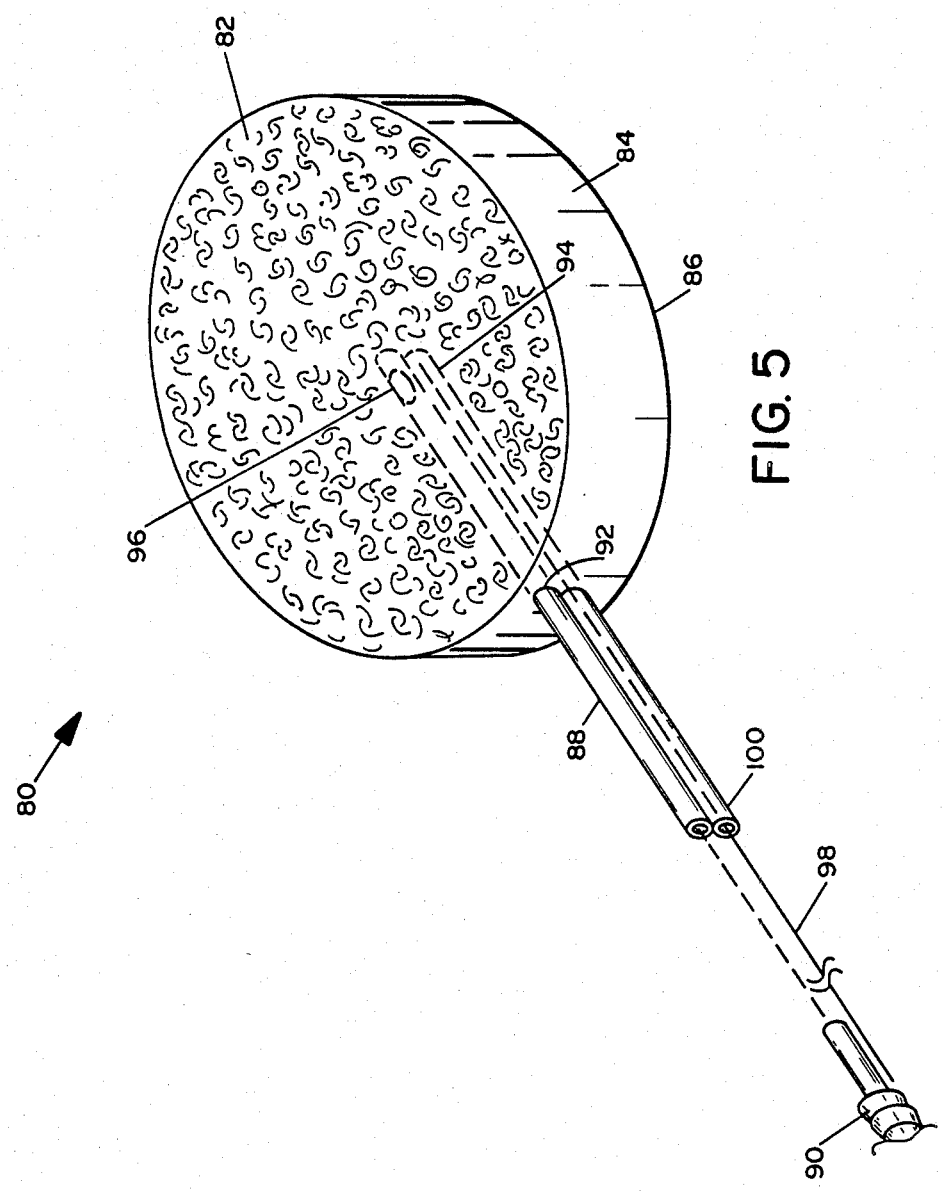

FIG. 5 illustrates a perspective view of a second alternative embodiment of a surgical suction mat 80 including a porous pliable material 82 such as a closely fibered synthetic member similar, for purposes of analogy by way of illustration only and not to be construed as limiting of the present invention, to that used as finely woven synthetic porous type of material, a synthetic coating about the finite height of the edge 84, a synthetic coating about the bottom 86, a suction tube 88 having a hose connection 90 at one end, extending through the finite edge 92, and terminating in the middle 94 of the mat with a geometrical flared suction end 96 as illustrated. A parallel wire 98-hose 100 is also provide.

The mode of operation is identical to that for the previous figures described as being based on the same theoretical concepts of fluid flow. While this alternative embodiment does not have a finite number of ports, it is interesting to note that the number of ports is considered to be infinite in number, and provides for suction at a finite point and in all directions therefrom. The geometrical shape of the porous member can assume a circular, rectangular, or any other predetermined geometrical shape as so desired.

Various modifications can be made to the present invention without departing from the apparent scope thereof. The pliable mat can be made from anylike material such as polyurethane, etc.

We claim:

1. A microsurgical suction mat comprising:
   a. pliable member means of a predetermined geometrical size;
   b. plurality of suction port means positioned in a predetermined geometrical configuration through said pliable member means for providing for passage of fluid through said pliable member means;
   c. geometrical member means provided for supporting exposed internal body organs such as arteries, nerves or the like extending upwardly from said pliable member means and about said suction port means;
   d. hose means including a plurality of holes corresponding to and aligned with said suction port means of said pliable member means providing for suction of fluid from said pliable member to a point distant from said pliable member means and secured to a bottom of said pliable member means.

2. Mat of claim 1 wherein said geometric member means comprises a porous member.

3. Mat of claim 1 wherein said geometric member means support means which comprises a plurality of parallel and spaced rib members aligned across said pliable member means and positioned perpendicular to said in line holes of said pliable member means.

4. Mat of claim 1 including a parallel hose joined to said hose means, said parallel hose means supporting a wire extending therethrough for maintaining geometrical memory on formation of said parallel hose supporting said wire.

5. Mat of claim 1 wherein said pliable member means is a silicone rubber material.

6. Mat of claim 1 wherein said pliable member means is a polyurethane material.

7. Mat of claim 1 wherein said pliable member means is blue in color.

8. Mat of claim 1 wherein a back side of said pliable member means is smooth.

9. Mat of claim 1 wherein said suction ports are in line.

10. Mat of claim 3 wherein said rib members support blood vessels.

11. A microsurgical suction mat for drainage of fluids during surgery comprising:
   a. pliable member including a rectangular geometrical shape;
   b. plurality of suction ports positioned in line through said pliable member for passage of fluids through said pliable member;
   c. suction hose having a plurality of holes corresponding to and aligned in line with said suction ports providing for suction of fluid through said suction ports to a point distant from said pliable member and secured to a bottom side of said pliable member; and,
   d. a plurality of spaced parallel ribs for supporting internal body organs extending upwardly from said pliable member and running perpendicular to said support holes, said parallel ribs being provided with spaces and gaps aiding in the flow of fluid to the suction ports; hose means including a plurality of holes corresponding to and aligned with said suction port means of said pliable member means providing for suction of fluid from said pliable member means to a point distant from said pliable member means and secured to a bottom of said pliable member means.

* * * * *